(12) United States Patent
Schroder

(10) Patent No.: US 6,864,478 B2
(45) Date of Patent: Mar. 8, 2005

(54) BEAM POSITION MONITORING FOR LASER EYE SURGERY

(75) Inventor: Russell Schroder, San Jose, CA (US)

(73) Assignee: VISX, Incorporation, Santa Clara, CA (US)

(*) Notice: Subject to any disclaimer, the term of this patent is extended or adjusted under 35 U.S.C. 154(b) by 281 days.

(21) Appl. No.: 10/128,130

(22) Filed: Apr. 22, 2002

(65) Prior Publication Data

US 2003/0197908 A1 Oct. 23, 2003

(51) Int. Cl.[7] .............................. H01J 3/14; A61B 18/18
(52) U.S. Cl. ............................ 250/234; 606/5; 606/11
(58) Field of Search ............................ 606/12, 4, 5, 10, 606/11; 250/201.1, 201.2, 234

(56) References Cited

U.S. PATENT DOCUMENTS

| | | | |
|---|---|---|---|
| 3,710,798 A | | 1/1973 | Bredemeier |
| 4,564,757 A | * | 1/1986 | LaBudde et al. ........... 250/239 |
| 5,122,135 A | | 6/1992 | Dürr et al. |
| 5,144,630 A | | 9/1992 | Lin |
| 5,162,641 A | * | 11/1992 | Fountain .................. 250/201.2 |
| 5,206,706 A | | 4/1993 | Quinn |
| 5,276,497 A | | 1/1994 | Oono |
| 5,350,374 A | * | 9/1994 | Smith ............................ 606/5 |
| 5,425,729 A | * | 6/1995 | Ishida et al. ................... 606/13 |
| 5,632,742 A | | 5/1997 | Frey et al. |
| 5,683,379 A | | 11/1997 | Hohla |
| 5,742,626 A | | 4/1998 | Mead et al. |
| 5,865,832 A | | 2/1999 | Knopp et al. |
| 5,997,141 A | | 12/1999 | Heacock |
| 6,322,216 B1 | | 11/2001 | Yee et al. |

FOREIGN PATENT DOCUMENTS

| | | |
|---|---|---|
| WO | WO 99/20173 | 4/1999 |
| WO | WO 99/23936 | 5/1999 |
| WO | WO 99/55216 | 11/1999 |
| WO | WO 01/10322 | 2/2001 |

OTHER PUBLICATIONS

Borsutzky et al., Tunable UV Radiation at Short Wavelengths (188–240nm) Generated by Sum–Frequency Mixing in Lithium Borate, *Appl. Phys.* B52, 380–384 (1991).

Talamo et al, (Eds.), The Excimer Manual: A clinician's guide to excimer laser surgery, Little, Brown & Company, 1997, Ch. 12.

* cited by examiner

*Primary Examiner*—Thanh X. Luu
(74) *Attorney, Agent, or Firm*—Townsend and Townsend and Crew LLP

(57) ABSTRACT

Improved methods, apparatus and systems for monitoring laser beam position enhance the safety and efficacy of laser eye surgery systems. The present invention will advantageously be used in laser eye surgery where accurate control of the laser beam is crucial for patient safety and successful vision correction. In one embodiment, a first beam of laser energy is directed through a scanning mechanism toward an eye to ablate the eye, and a second beam of laser energy is directed through the scanning mechanism toward a sensor. When the scanning mechanism is moved by a laser eye surgery system to move the first beam across the eye, the scanning mechanism also moves the second beam across the sensor. Movement of the beam across the sensor can be used to monitor movement of the first beam across the eye. If actual movement of the first beam across the eye does not match desired movement of the beam, one or more components of the laser surgery system will shut down in order to stop the laser eye surgery procedure, thus preventing undesirable ablation of the eye.

24 Claims, 7 Drawing Sheets

BEAM POSITION MONITORING FOR LASER EYE SURGERY

BACKGROUND OF THE INVENTION

The present invention relates generally to methods, apparatus and systems for performing laser eye surgery. More particularly, the present invention relates to laser beam position monitoring methods, apparatus and systems for enhancing safety of laser eye surgery systems.

Photorefractive keratectomy (PRK) and phototherapeutic keratectomy (PTK) employ laser beam delivery systems for directing laser energy to a patient's eye to selectively ablate corneal tissue to reform or sculpt the shape of the cornea and, thereby, to improve vision. Present commercial systems often employ excimer lasers. In a first type of system, positioning of the beam is generally fixed and the beam has a cross-sectional area generally corresponding to an entire surface area of a surgical site on the cornea. Cross-sectional portions of the beam are then sequentially masked or adjusted so as to selectively vary the amount of energy exposure of different portions of the surgical site so as to effect the desired sculpting. This can typically be achieved by using an iris or other exposure control mechanism. While highly effective and relatively easy to control, employing a laser beam having a cross-sectional area generally equal to the area of the treatment or surgical site (typically having a diameter of 5.0 mm to 10.0 mm) often involves the use of relatively large amounts of energy. This is typically relatively expensive, and leads to relatively large laser systems.

As an alternative to such large beam diameter systems, laser "scanning" systems can be employed for corneal ablation. Such scanning systems typically employ a laser beam having a smaller cross-sectional area, thereby decreasing energy requirements. Accordingly, laser scanning systems delivering laser beams of relatively small cross-sectional area can be more economic to use and normally are of smaller construction than laser systems having larger diameter beams. However, the use of such small beams complicates certain aspects of the treatment protocols required to perform the sculpting. For example, to achieve a desired level of volumetric tissue removal or ablation from the eye, the treatment beam is scanned over or otherwise moved across the eye from one position to a next during the surgical procedure. Movement of the beam is typically achieved through motorized scanning mechanisms, devices, or the like. These scanning mechanisms often regulate the position of an optical element, such as the angle of a mirrored surface, the lateral position of an offset imaging lens or the like, so as to adjust the lateral position of the beam across the treatment site. In a related type of system, the laser beam is scanned over the corneal surface while varying the cross-section of the laser beam.

To achieve properly controlled laser exposure over the entire treatment site on the eye, the positioning of a scanning laser beam should be controlled accurately. If the beam resides at one position for too long, due to a jam or malfunction of the scanning mechanism for example, the desired tissue ablation pattern may not be achieved. A jam of the scanning system may jeopardize the success of the surgery and could cause damage to the patient's eye. Since the laser beam itself is not easily visible, malfunction of some scanning mechanisms may not be readily detectable by an observer.

Thus, it would be desirable to provide methods, apparatus and/or systems for monitoring a laser beam position in a laser surgery system. It would also be desirable to verify that a laser beam position matches a desired beam position and to stop a laser surgery procedure if the beam position does not match the desired position. Preferably, such methods, apparatus and the like could be incorporated into a laser surgery system in a cost-effective manner without interfering with performance of the system. Though such methods, apparatus or subsystems would find particular use in scanning laser beam systems, they may also feasibly be used with large diameter laser beam systems.

BRIEF SUMMARY OF THE INVENTION

The present invention provides methods, apparatus and systems for monitoring the position of a laser beam during laser eye surgery. Typically, the invention is used to verify that a desired scanning or adjustment of the laser beam across an eye is, in fact, occurring. Such monitoring and verification functions enhance the safety and success of laser eye surgery procedures. Generally, the invention includes a monitoring laser beam directed through a scanning mechanism at a sensor. When the scanning mechanism is adjusted, to scan an ablative laser beam across an eye, the scanning mechanism also scans the monitoring laser beam across the sensor. Changes in position of the monitoring beam sensed by the sensor can be used to measure scanning of the ablative beam across the eye. Such measured scanning may then be compared to a desired scanning pattern and, if the actual scanning does not match the desired pattern, the laser surgery system may shut down to halt the laser surgery procedure at least temporarily and inhibit unwanted ablation of the eye.

In one aspect of the present invention, a method for monitoring scanning of a laser eye surgery system includes directing a first beam of laser energy along a first axis toward a first location on an eye using a scanning optical element, and directing a second beam of laser energy at the scanning optical element along a second axis, the scanning optical element transmitting the second beam toward a sensor. The method further includes moving the scanning optical element to scan the first beam to a second location on the eye, and sensing movement of the scanning optical element with the sensor.

Optionally, the method also includes determining a desired scanning sequence for sequentially scanning the first beam, scanning the first beam with the scanning optical element in accordance with the desired scanning sequence, and comparing the actual scanning with the desired scanning sequence. In this embodiment, the method of the present invention may further include interrupting the first beam when the actual scanning of the first beam deviates from the desired scanning sequence. In another embodiment, the step of determining a desired scanning sequence includes entering a patient specific parameter into a computer and causing the computer to determine the desired scanning sequence. Optionally, an adjustment mechanism may be operatively linked to the computer and to the scanning optic element and the method of the invention may include transmitting instructions from the computer to the adjustment mechanism to cause the adjustment mechanism move the scanning optic element.

In some embodiments, the scanning optic element includes at least one mirror having at least one reflective surface. In those embodiments, the first and second beams may be directed at a first reflective side of the mirror. For example, the first beam may be directed at the first reflective side at a 45 degree angle and the second beam may be directed at the first reflective side at an angle less than 45 degrees. In other embodiments, the mirror of the scanning optical element includes a first reflective side and a second reflective side. In such embodiments, the first beam may be directed at the first reflective side and the second beam may be directed at the second reflective side, or vice versa. In yet other embodiments, two mirrors might be used and might be disposed at an angle of about 90 degrees in relation to each other. In that case, the first beam is directed at a first mirror and the second beam is directed at a second mirror. In still another embodiment, the scanning optical element comprises a lens.

Generally, a laser beam sensor according to the present invention may be any device or component suitable for sensing laser energy. In one embodiment, for example, a sensor comprises one or more position-sensing photo diodes. Such an embodiment may employ one diode or multiple diodes. In one embodiment, multiple position-sensing photo diodes are disposed in a pattern on a substrate.

In another aspect of the present invention, a system for monitoring scanning of a laser eye surgery system for laser treatment of an eye includes at least one movable scanning optical element, a laser beam sensor, a first laser beam source and a second laser beam source. The first laser source is generally for directing a first laser beam at the scanning optical element along a first axis, the scanning optical element positioned for transmitting the first beam toward the eye. The second laser beam source is generally for directing a second laser beam along a second axis toward the scanning optical element so that the scanning optical element transmits the second beam toward the laser beam sensor during treatment of the eye.

Optionally, the system may further include a laser beam adjustment mechanism for moving the scanning optical element. Also optionally, the system may include a computer programmed to effect a desired scanning sequence for sequentially moving the scanning optical element. The computer, in turn, may be programmed to determine the desired scanning sequence upon entry of a patient eye specific parameter into the computer. As previously described, the scanning optical element may be a lens or one or more mirrors with one or more reflective surfaces, in any of a number of various configurations and combinations.

In yet another aspect, an apparatus for monitoring scanning of a laser eye surgery system for laser treatment of an eye includes a laser beam source and a laser beam sensor. The laser beam source directs a laser beam through a scanning optical element of a laser surgery system so that the scanning optical element transmits the laser beam toward the laser beam sensor during treatment of the eye.

DETAILED DESCRIPTION OF THE INVENTION

The present invention provides methods, apparatus and subsystems for monitoring laser beam position in laser eye surgery systems, particularly though not exclusively in laser eye surgery systems of the scanning type. In particular, the present invention provides monitoring methods and systems for verifying laser beam position during the course of corrective surgical ablation of an eye. By verifying that the ablative laser beam has moved to a position corresponding with a predetermined position dictated by a predetermined adjustment sequence or ablation pattern, the system can verify that mechanisms used to scan or move the beam from one position to a next position are functioning properly. This monitoring function enhances safety and efficacy of the laser surgery system by enabling the system to detect malfunctions in, for example, the scanning mechanism, and to interrupt the surgical procedure when an actual laser beam position does not correspond with a corresponding position dictated by the predetermined adjustment sequence.

By "scanning," it is meant that an ablative laser beam is moved successively from one lateral position to a next lateral position across the treatment site on an eye so as to expose successive portions of the eye to a predetermined amount or dosage of laser energy. Usually, the laser system will be operated in a pulsed manner and the exposure at any particular position will result from a number of pulses which occur over a very short time period. The corrective eye procedure is normally completed when the ablative laser beam has completed the scanning sequence in accordance with a predetermined ablation pattern.

Figure 1:
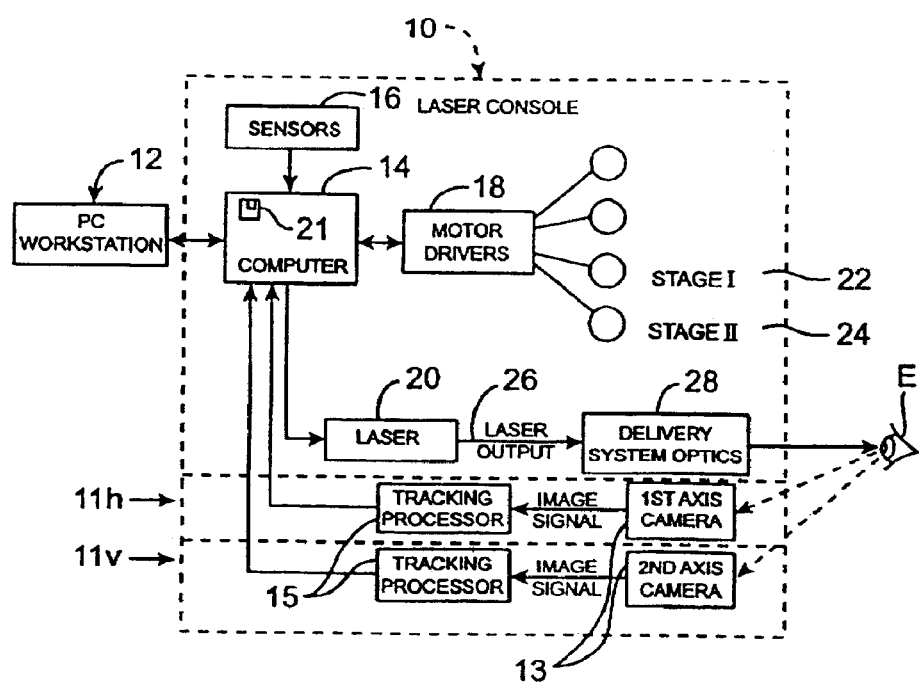
FIG. 1 is a simplified block diagram of a laser eye surgery system with which various embodiments of the present invention may be incorporated.

Referring now to FIG. 1, a laser eye surgery system 10 with which monitoring methods, apparatus and subsystems of the present invention may be used is similar to a laser eye surgery system described in U.S. Pat. No. 6,322,216 B1, assigned to the assignee of the present invention, the entire contents of which is hereby incorporated by reference. System suitably includes a laser 20 which generates a laser beam 26 that is selectively directed toward eye E by delivery system optics 28, a personal computer workstation 12 coupled to a computer 14 with a tangible medium 21, and horizontal and vertical trackers 11h, 11v, each of which includes a camera 13 and an associated tracking processor 15. Delivery system optics 28 scan beam 26 over eye E according to instructions from computer 14. Computer 14 generally scans beam 26 over eye E by changing the angular position of first and second stage pivot systems 22, 24. In alternative embodiments, the computer may scan the beam by pivoting one or more mirrors using galvanometric motors, or any of a wide variety of alternative scanning mechanisms. Optionally, computer 14 may direct profiling of beam 26 using one or more variable apertures. Further details of laser eye surgery system 10 may be found in U.S. Pat. No. 6,322,216 B1.

Ideally, methods, apparatus and subsystems of the present invention are suitable for integration into VISX STAR™ and VISX STAR S2™ laser eye surgery systems, which are commercially available from VISX, Incorporated of Santa Clara, Calif. Alternatively, any other suitable laser eye surgery system may be used, such as but not limited to laser systems commercially available from Chiron Vision of Irvine, Calif. (a division of Bausch & Lomb); Nidek Co., Ltd. of Gamagori, Japan; Laser Sight, Inc. of Orlando, Fla.; Autonomous Technologies Corporation of Orlando, Fla.; and a variety of others.

Laser 20 may include, but is not limited to, an excimer laser such as an argon-fluoride excimer laser producing laser energy with a wavelength of about 193 nm. Alternative laser systems may include solid state lasers, such as frequency multiplied solid state lasers, flash-lamp and diode pumped solid state lasers, and the like. Exemplary solid state lasers include UV solid state lasers producing wavelengths of approximately 188–240 nm such as those disclosed in U.S. Pat. Ser. Nos. 5,144,630, and 5,742,626; and in Borsuztky et al., *Tunable UV Radiation at Short Wavelengths (188–240 nm) Generated by Frequency Mixing in Lithium Borate*, Appl. Phys. 61:529–532 (1995). A variety of alternative lasers might also be used. The laser energy will generally comprise a beam formed as a series of discreet laser pulses, and the pulses may be separated into a plurality of beamlets.

Figure 2:
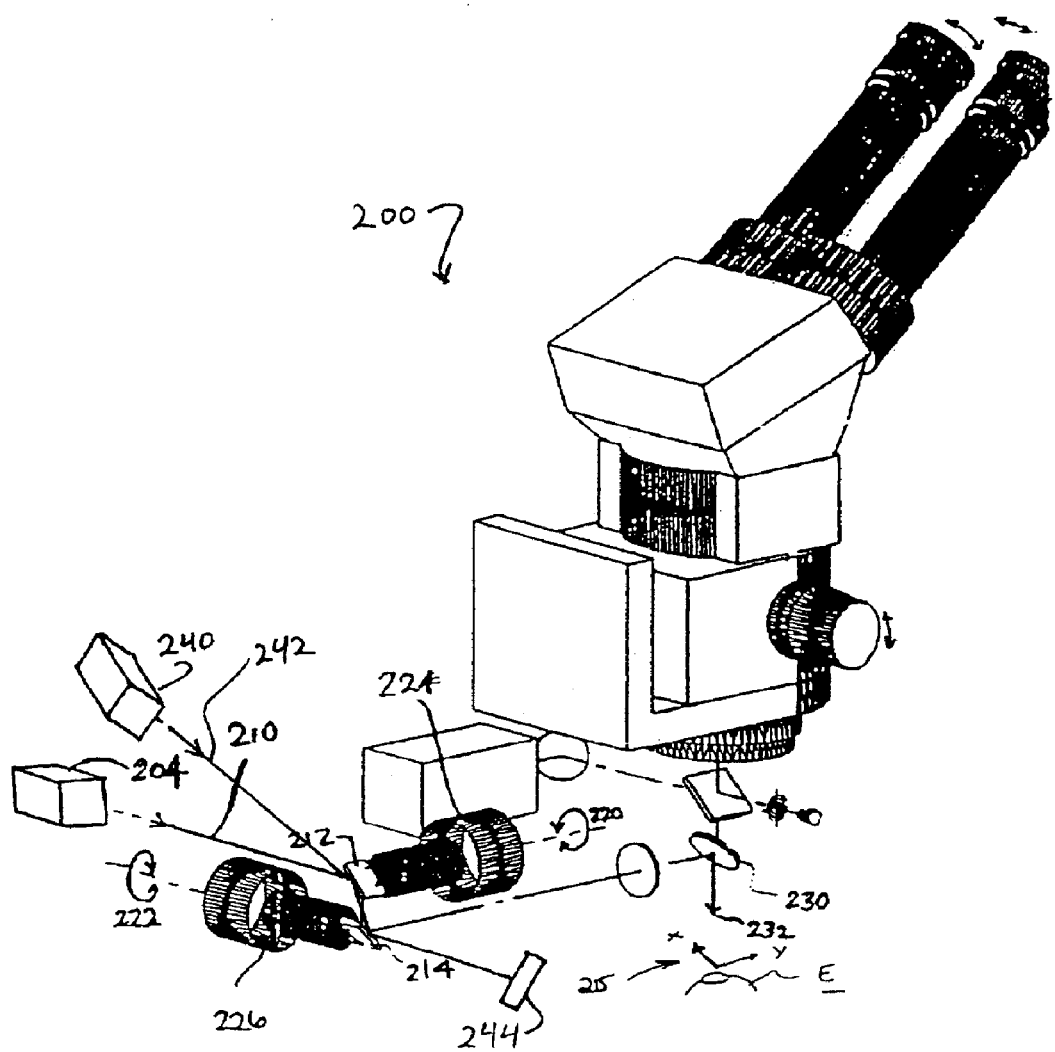
FIG. 2 is a simplified perspective view of an optical train of a laser surgery system including one embodiment of the present invention.

Referring now to FIG. 2, a scanning laser surgery system 200 with which laser beam monitoring methods and apparatus of the present invention may be used is similar to the system described in International Patent Application Publication Number WO 01/10322 A1, assigned to the assignee of the present invention, the entire contents of which are hereby incorporated by reference. Laser surgery system 200 suitably includes a first laser beam source 204 for directing an ablative laser beam 210 at an eye E and a monitoring laser beam source 240 for directing a second laser beam 242 at a laser beam sensor 244. System 200 also includes a scanning element 212, 214 for directing ablative laser beam 210 and through which both ablative laser beam 210 and monitoring laser beam 242 pass.

In the embodiment depicted in FIG. 2, scanning element 212, 214 comprises a first reflective surface 212 and a second reflective surface 214. Reflective surfaces 212, 214 are angularly adjustable, as indicated by arrows 220 and 222, to scan ablative laser beam 210 across a treatment area on eye E. Reflecting surfaces 212, 214 are operatively associated with adjustment mechanisms 224, 226, respectively, which are typically in the form of motorized devices such as galvos. Rotating reflecting surface 212 by galvo 224 varies the position of laser beam 210 along an X-axis while rotation of reflecting surface 214 varies the position of laser beam 210 along a Y-axis, with reference to an X-Y coordinate reference frame 215.

In various other embodiments, as will be described more fully below, scanning element 212, 214 may generally comprise any suitable mechanism for scanning a laser beam across an eye. In some embodiments, for example, a scanning element includes one or more mirrors each having one or more reflective surfaces. In other embodiments, a scanning element comprises an optical element, such as a lens. Typically, any of these scanning elements may be moved or adjusted in one or more directions to scan an ablative beam across an eye. For example, in various embodiments a scanning element may be adjusted vertically, adjusted horizontally, turned on an axis, and/or the like. The methods, apparatus and systems of the present invention generally provide a second laser beam source, such as source 240, to direct a monitoring laser beam through a scanning element to a sensor, to monitor movement of the scanning element.

Figure 3A:
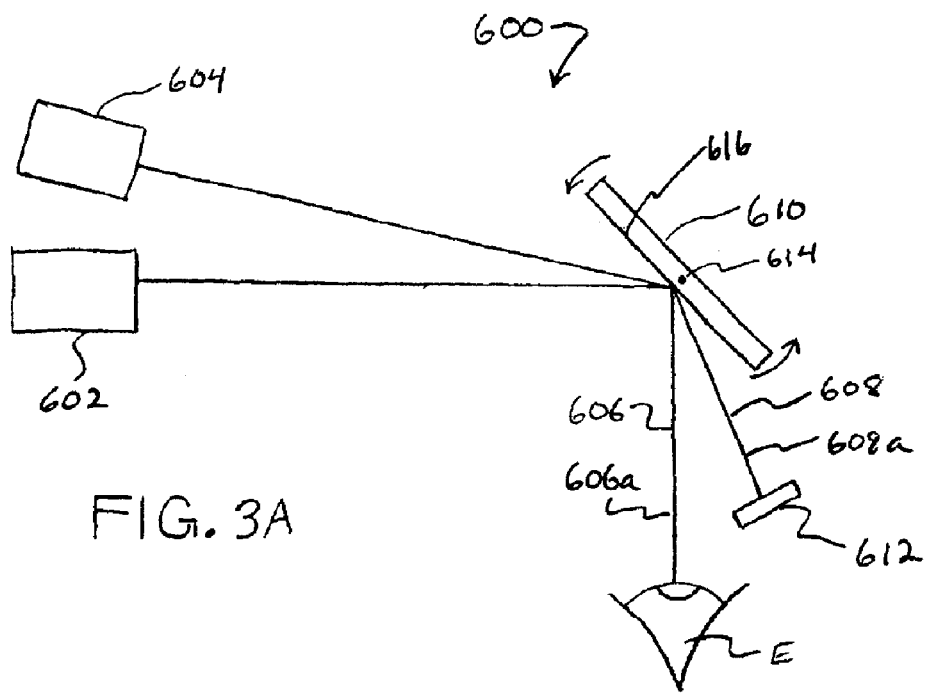
FIGS. 3A and 3B are schematic side views of a scanning and monitoring system according to an embodiment of the present invention.
Figure 3B:
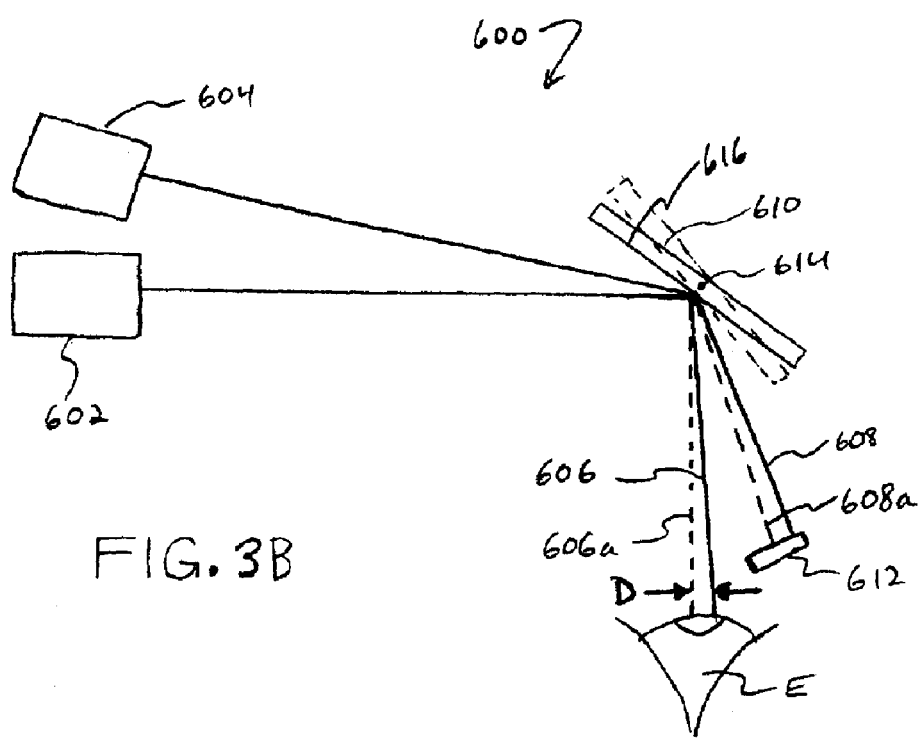

With reference now to FIGS. 3A and 3B, one embodiment of a laser beam scanning and monitoring system 600 suitably includes a first laser beam source 602 providing a first beam 606 with a first initial beam axis 606*a* directed at an eye E, and a second laser beam source 604 providing a second beam 608 with a second initial beam axis 608*a* directed at a sensor 612. A scanning element 610 for directing first beam 606 and second beam 608 includes a mirror with a reflective surface 616 and an axis 614.

Generally, scanning element 610 may be moved in any suitable manner to scan first beam across eye E. For example, scanning element 610 may be pivoted about axis 614, as shown by arrows in FIG. 3A. Alternatively, scanning element 610 may be pivoted about two or more axes, may be moved horizontally or vertically towards and away from first laser beam source 602 and/or towards and away from eye E, or in any other suitable direction. Furthermore, first beam 606 and second beam 608 may be directed at scanning element 610 from a variety of different angles. For example, in one embodiment first beam 606 may be directed at reflective surface 616 at an angle of about 45 degrees second beam 608 may be directed at reflective surface 616 at an angle less than about 45 degrees. In another embodiment, second beam 608 may be directed at reflective surface 616 at an angle greater than about 45 degrees.

As described above, scanning element 610 may assume any of a number of suitable configurations. For example, multiple mirrors may be included, multiple reflective surfaces on one or more mirrors may be included, mirrors may be oriented at two or more angles, and/or the like. Typically, methods and apparatus of the present invention will utilize wholly reflective surfaces for directing first beam 606, rather than partially reflective surfaces. This provides the advantage of not reducing the power of the ablating first beam. However, various embodiments of the present invention may incorporate a partially reflective surface, such as a partially silvered mirror, to direct one or more laser beams.

Figure 3C:
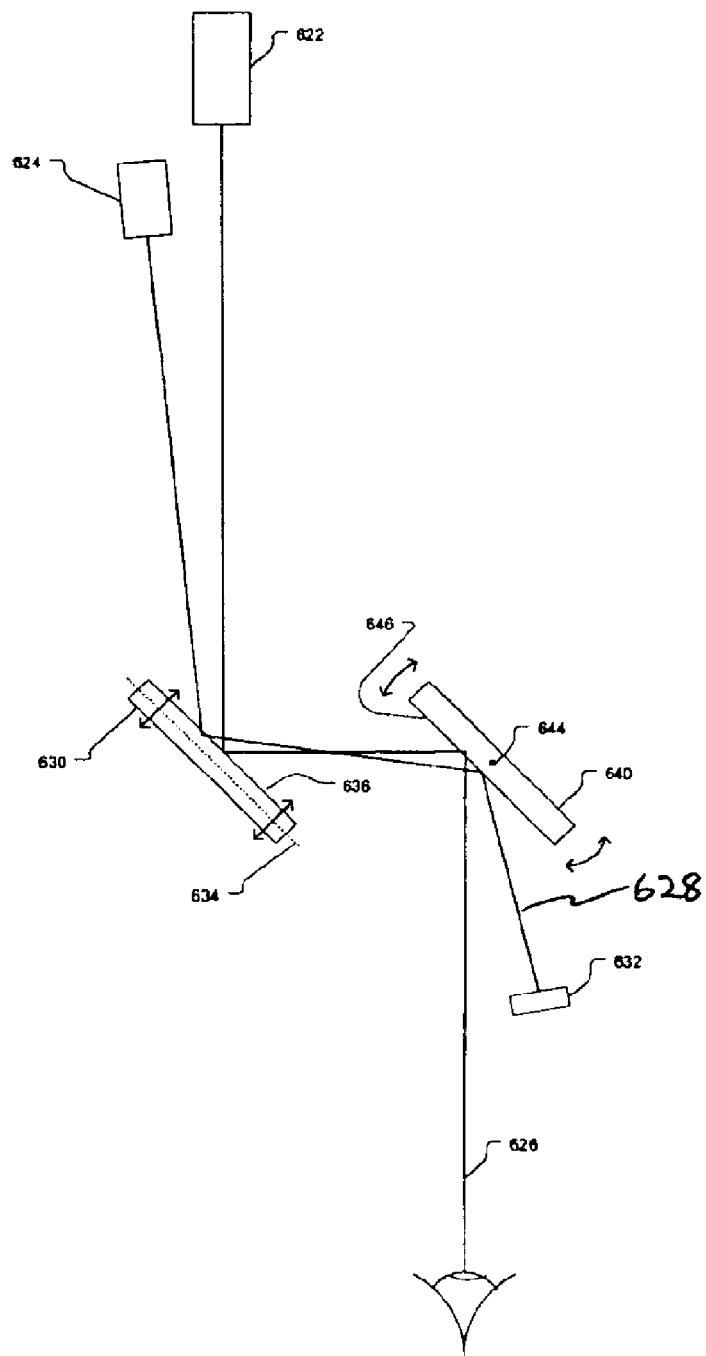

For example, and with reference now to FIG. 3C, an alternative embodiment of a laser beam scanning and monitoring system 620 suitably includes a first laser beam source 622 providing a first beam 626 directed at an eye E, and a second laser beam source 624 providing a second beam 628 directed at a sensor 632. A scanning element for directing first beam 626 and second beam 628 includes a first mirror 630, having a first reflective surface 636 and a first axis of rotation 634, and a second mirror 640, having a second reflective surface 646 and a second axis of rotation 644. In this embodiment, first axis of rotation 634 is approximately horizontal or parallel to the page on which FIG. 3C is drawn, while second axis of rotation 644 is approximately vertical or perpendicular with the page on which FIG. 3C is drawn. Thus, the first and second axes 634, 644 are disposed at approximately a 90° angle relative to one another.

FIG. 3B illustrates scanning of first beam 606 to a new position on eye E. When first beam 606 is scanned to a new location on eye E, second beam 608 is simultaneously scanned to a new position on sensor 612. Initial positions of first beam 606 and second beam 608 are shown by dotted lines depicting first initial axis 606*a* and second initial axis 608*a*. By sensing change in position of second beam 608, sensor 612 may be used to measure movement of first beam 606 across eye E. For example, in one embodiment, the distance of movement of second beam 608 across sensor 612 may correspond directly to distance D of movement of first beam 606 across eye E. In another embodiment, movement of second beam 608 across sensor 612 may be proportional to movement of first beam 606 across eye E. In some embodiments, sensor 612 may be configured to itself provide measurement of movement of first beam 606 across eye E. In other embodiments, sensor 612 may be coupled to a computer, such as computer 14 depicted in FIG. 1, and data sensed by sensor 612 may be transmitted to computer 14 where the data is processed to measure movement of first beam across eye E.

In accordance with one aspect of the present invention, movement of second beam 608 across sensor 612 may be compared to expected movement of second beam 608 across sensor 612, to monitor a laser eye surgery procedure. For example, a desired scanning pattern for an eye may be entered into a computer such as computer 14 in FIG. 1, or computer 14 may calculate a desired scanning pattern, based on measurements of a treatment area, refractive correction parameters and/or the like. The scanning pattern on the eye will generally correlate to a scanning pattern of second beam 608 across sensor 612. Computer 14 will be configured to receive data sensed my sensor 612 and to determine if the actual scanning pattern across eye is the same as the desired scanning pattern. Typically, if computer 14 detects a variation between the actual and desired scanning patterns, computer 14 is configured to stop a laser surgery procedure, for example by shutting down, at least temporarily, one or more components of the laser surgery system.

Thus, the laser beam scanning and monitoring systems and methods of the present invention provide enhanced safety for laser surgery systems. Another advantage of the present invention is that using two laser beam sources and two beams provides monitoring and safety functions without diminishing power of the beam directed towards the eye for ablation. Furthermore, because the monitoring apparatus—generally the second laser beam source and the sensor—is independent, many different configurations of the second laser source and the sensor can be used without interfering with other components of a system for laser eye surgery.

According to one aspect of the present invention, sensors used in various embodiments of the present invention may comprise any of a number of suitable sensors for detecting movement of a laser beam. For example, in one embodiment, a dual-axis, duo-lateral position sensing photo diode such as a PSS-DL-100 Cer, available from Pacific Silicon Sensors, Inc., of Westlake Village, Calif., may be used. In other embodiments, sensors like those described in copending Patent Application Publication No. WO 01/10322 A1, previously incorporated herein by reference, may be used. Sensors described in that application generally include one or more masks disposed over a photosensitive surface. When a laser beam, or a portion of a laser beam crosses from a masked area into an unmasked area, the photosensitive surface senses the beam. Thus, the sensor may be used to detect movement of the beam and/or to detect whether the beam is moved in a desired pattern. In yet another embodiment, a sensor may comprise a quadrant sensor, wherein four separate sensors are used to sense four quadrants of a scanning area. In fact, multiple sensors may be used in various other embodiments and configurations.

Figure 4A:
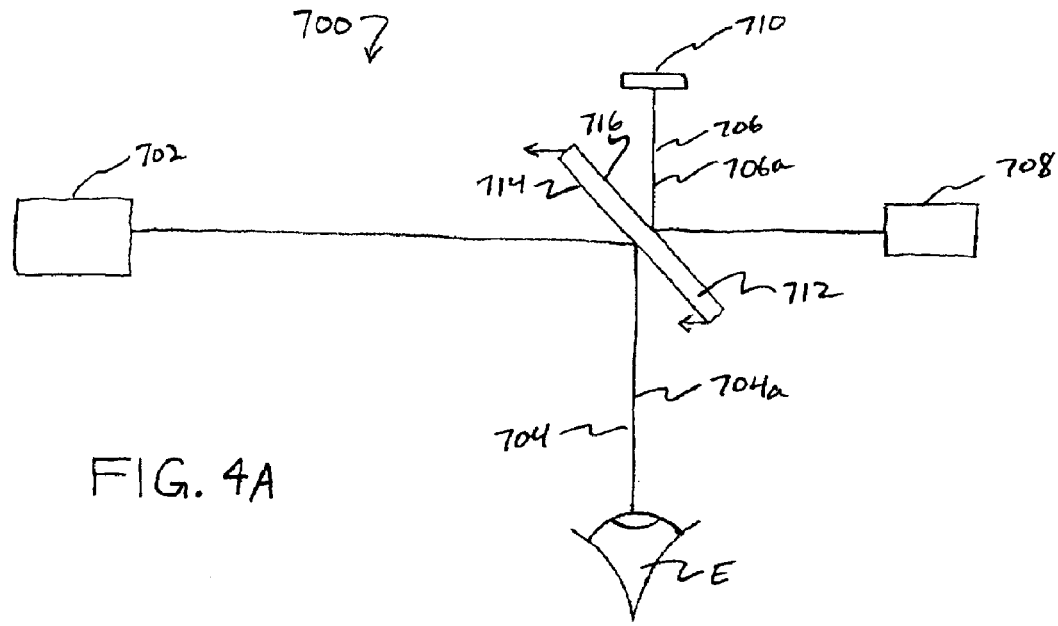
FIGS. 4A and 4B are schematic side views of a scanning and monitoring system according to another embodiment of the present invention.
Figure 4B:
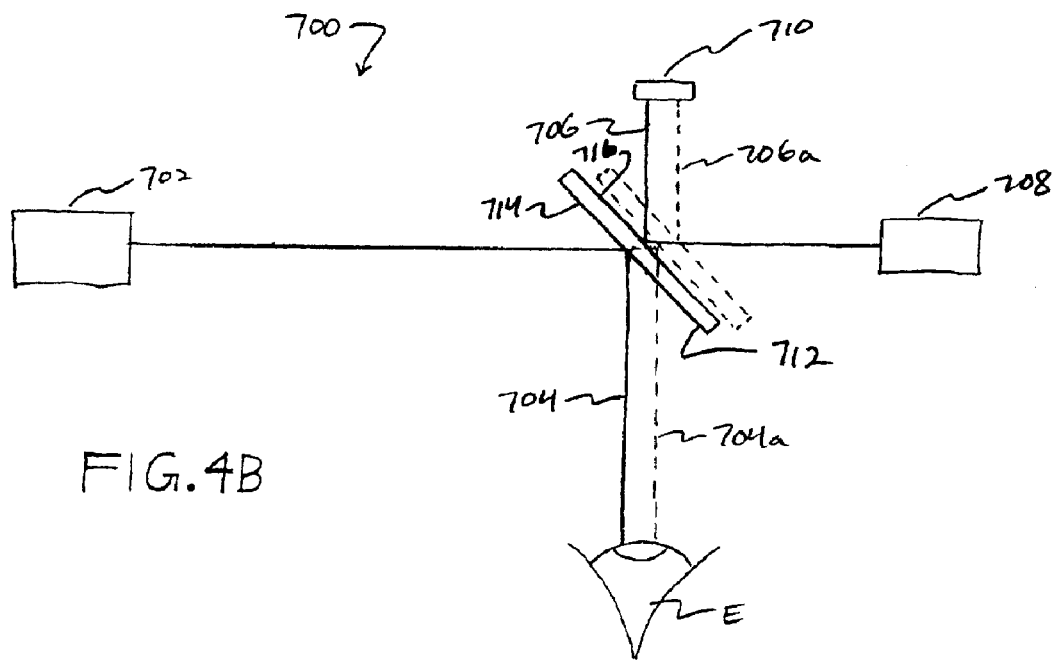

Referring now to FIGS. 4A and 4B, another embodiment of a laser beam scanning and monitoring system 700 suitably includes a first laser beam source 702 providing a first beam 704 with a first initial beam axis 704a directed at an eye E, and a second laser beam source 708 providing a second beam 706 with a second initial beam axis 706a directed at a sensor 710. A scanning element 712 includes a mirror with a first reflective surface 714 for directing first beam 704 towards eye E and a second reflective surface 716 for directing and second beam 706 toward sensor 710.

Scanning element 712 may be moved in any of a variety of suitable directions by a laser surgery system. In FIGS. 4A and 4B, scanning element 712 is shown moving towards first laser source 702, however, in this or other embodiments scanning element 712 may move vertically, about one or more axes and/or the like. As with the embodiments described above, movement of scanning element 712 is detected by sensor 710 as movement of second beam 706 across sensor 710. This movement can then be used to monitor scanning of first beam 704 across eye E and, thus, to enhance safety of a laser surgery system.

Figure 5:
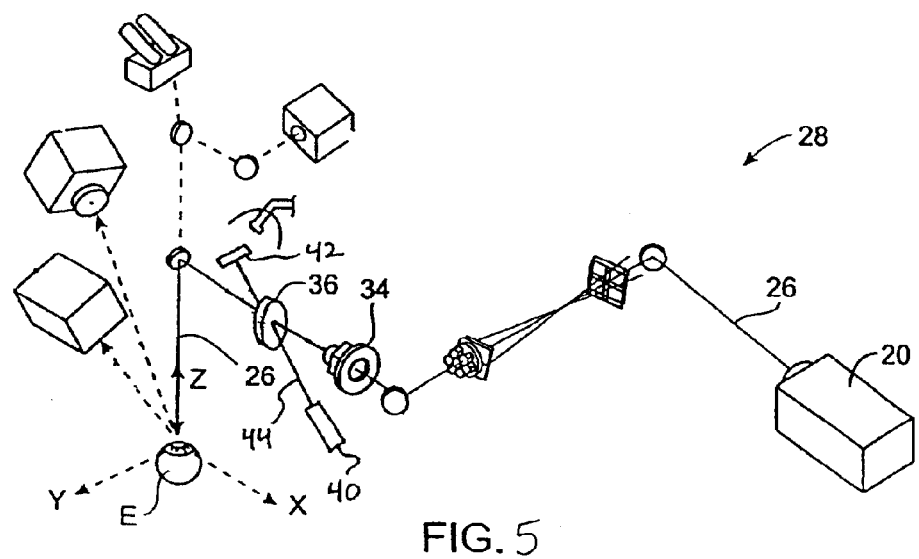
FIG. 5 is a simplified perspective view of the laser delivery optics and tracking imaging axes of a laser surgery system including one embodiment of the present invention.

Referring now to FIG. 5, typical delivery system optics 28 for a laser surgery system having a scanning mechanism 36 comprising one or more lenses are illustrated without their associated support structure. The embodiment in FIG. 5 is similar to a laser eye surgery system described in detail in U.S. Pat. Ser. No. 6,322,216 B1, previously incorporated herein by reference. The system of FIG. 5, however, includes first laser beam source 20 for directing an ablative laser beam 26 through scanning mechanism 36 at an eye E, and a second laser beam source 40 for directing a monitoring laser beam 44 through scanning mechanism 36 to a sensor 42. As described above in reference to other embodiments, scanning mechanism 36 will laterally deflect ablative beam 26 across eye E in the X-Y plane and will also laterally deflect monitoring beam 44 across sensor 42 in the X-Y plane. Movements of monitoring beam 44 sensed by sensor 42 can be used to monitor movements of ablative beam across eye E.

Figure 6A:
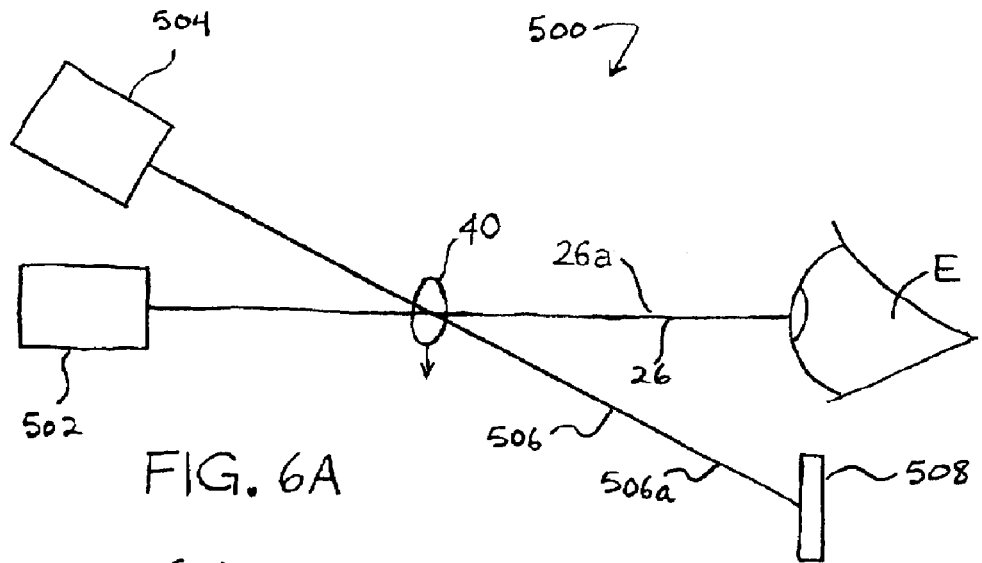
FIGS. 6A and 6B are schematic side views of a scanning and monitoring system for use with a system as in FIG. 5 according to an embodiment of the present invention.
Figure 6B:
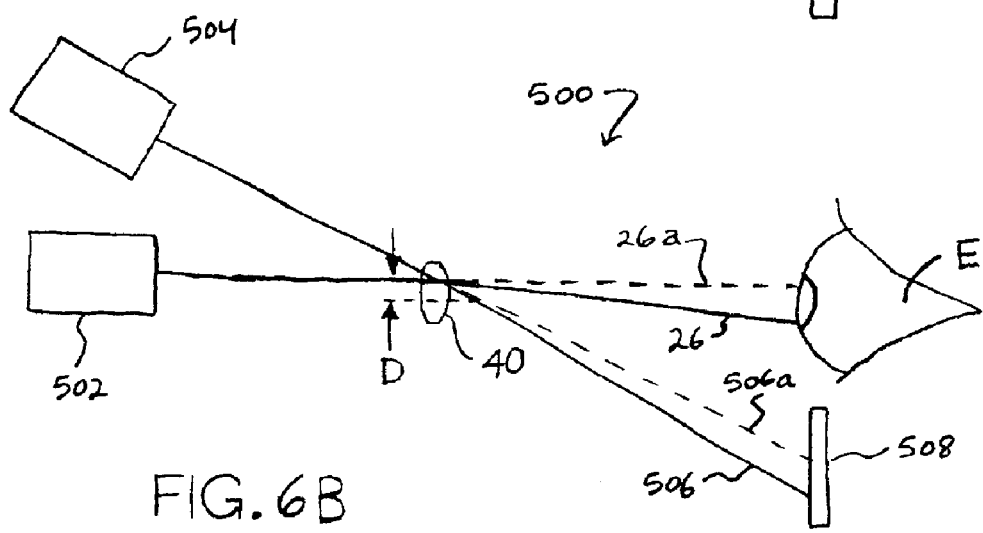

Referring now to FIGS. 6A and 6B, yet another embodiment of a laser beam scanning and monitoring system 500 suitably includes a first laser beam source 504 providing a first beam 26 with a first initial beam axis 26a directed at an eye E, and a second laser beam source 504 providing a second beam 506 with a second initial beam axis 506a directed at a sensor 508. A scanning element 40 for directing first beam 26 and second beam 506 comprises an imaging lens which may be displaced from an initial beam axis 26a by a distance D. For further details of scanning elements including lenses, again refer to U.S. Pat. Ser. No. 6,322,216 B1, previously incorporated herein by reference. Generally, when scanning element 40 is moved to scan first beam 26 across eye E, it also scan second beam 506 across sensor 508. As described in reference to various embodiments above, scanning of the first beam 26 across eye E may thus be monitored by scanning of second beam 506 across sensor 508.

While the above is a complete description of the preferred embodiments of the invention, various alternatives, modifications, and equivalents may be used. For example, in alternative embodiments, multiple monitoring laser beams and/or sensors may be used to monitor scanning of an ablative beam across an eye. Additionally, scanning systems not described above or not yet conceived may be monitored using methods, apparatus and/or subsystems of the present invention and such uses are contemplated within the scope of the invention. Thus, the above description should not be taken as limiting the scope of the invention which is defined by the appended claims.

What is claimed is:

1. A method for monitoring scanning of a laser eye surgery system, the method comprising:
   directing a first beam of laser energy along a first axis toward a first location on an eye using a scanning optical element;
   directing a second beam of laser energy at the scanning optical element along a second axis, the scanning optical element transmitting the second beam toward a sensor;
   moving the scanning optical element to scan the first beans to a second location on the eye;

sensing movement of the scanning optical element with the sensor;

determining a desired scanning sequence for sequentially scanning the first beam;

scanning the first beam with the scanning optical element in accordance with the desired scanning sequence; and comparing the actual scanning with the desired scanning sequence.

2. A method as in claim 1, further comprising interrupting the first beam when the actual scanning of the first beam deviates from the desired scanning sequence.

3. A method as in claim 1, wherein the determining step includes entering a patient specific parameter into a computer and causing the computer to determine the desired scanning sequence.

4. A method as in claim 3, wherein an adjustment mechanism is operatively linked to the computer and to the scanning optic element, the method including transmitting instructions from the computer to the adjustment mechanism to cause the adjustment mechanism move the scanning optic element.

5. A method as in claim 1, wherein the scanning optic element comprises at least one mirror having at least one reflective surface.

6. A method as in claim 5, wherein the first and second beams are directed at a first reflective side of the mirror.

7. A method as in claim 6, wherein the first beam is directed at the first reflective side at a 45 degree angle and the second beam is directed at the first reflective side at an angle less than 45 degrees.

8. A method as in claim 5, wherein the at least one mirror includes a first reflective side and a second reflective side, the first beam being directed at the first reflective side and the second beam being directed at the second reflective side.

9. A method as in claim 5, wherein the at least one mirror comprises a first mirror having a first axis of rotation and a second mirror having a second axis of rotation disposed at a 90 degree angle relative to the first axis of rotation.

10. A method as in claim 9, wherein the first beam is directed at the first mirror and the second beam is directed at the second mirror.

11. A method as in claim 1, wherein the scanning optical element comprises a lens.

12. A method as in claim 1, wherein the sensor comprises at least one position-sensing photo diode.

13. A method as in claim 12, wherein the at least one position-sensing photo diode comprises multiple position-sensing photo diodes disposed in a pattern on a substrate.

14. A system for monitoring scanning of a laser eye surgery system for laser treatment of an eye, the system comprising:

at least one movable scanning optical element comprising at least one mirror having at least one reflective surface;

a laser beam sensor;

a first laser beam source directing a first laser beam at the scanning optical element along a first axis, the scanning optical element positioned for transmitting the first beam toward the eye; and a second laser beam source directing a second laser beam along a second axis toward the scanning optical element so that the scanning optical element transmits the second beam toward the laser beam sensor during treatment of the eye, wherein the first and second beams are directed at a first reflective side of the mirror.

15. A system as in claim 14, further comprising a laser beam adjustment mechanism for moving the scanning optical element.

16. A system as in claim 15, further comprising a computer programmed to effect a desired scanning sequence for sequentially moving the scanning optical element.

17. A system as in claim 16, wherein the computer is programmed to determine the desired scanning sequence upon entry of a patient eye specific parameter into the computer.

18. A system as in claim 14, wherein the first beam is directed at the first reflective side at a 45 degree angle and the second beam is directed at the first reflective side at an angle less than 45 degrees.

19. A system as in claim 14, wherein the at least one mirror includes a first reflective side and a second reflective side, the first beam being directed at the first reflective side and the second beam being directed at the second reflective side.

20. A system as in claim 14, wherein the at least one mirror comprises a first mirror having a first axis of rotation and a second mirror having a second axis of rotation disposed at a 90 degree angle relative to the first axis of rotation.

21. A system as in claim 20, wherein the first beam is directed at the first mirror and the second beam is directed at the second mirror.

22. A system as in claim 14, wherein the sensor comprises at least one position-sensing photo diode.

23. A system as in claim 22 wherein the at least one position-sensing photo diode comprises multiple position-sensing photo diodes disposed in a pattern on a substrate.

24. A system for monitoring scanning of a laser eye surgery system for laser treatment of an eye, the system comprising:

at least one movable scanning optical element comprising a lens;

a laser beam sensor;

a first laser beam source directing a first laser beam at the scanning optical element along a first axis, the scanning optical element positioned fan transmitting the first beam toward the eye; and a second laser beam source directing a second laser beam along a second axis toward the scanning optical element so that the scanning optical element transmits the second beam toward the laser beam sensor during treatment of the eye, wherein the first and second beams are directed at a first side of the lens.

* * * * *